(12) United States Patent
Martin et al.

(10) Patent No.: US 6,500,476 B1
(45) Date of Patent: Dec. 31, 2002

(54) PRESERVATION COMPOSITIONS AND PROCESS FOR MUSHROOMS

(75) Inventors: Stefan T. Martin, Flourtown, PA (US); Howard S. Kravitz, Wayne, PA (US); William R. Romig, Morrestown, NJ (US)

(73) Assignee: EPL Technologies, Inc., Philadelphia, PA (US)

( * ) Notice: Subject to any disclaimer, the term of this patent is extended or adjusted under 35 U.S.C. 154(b) by 0 days.

(21) Appl. No.: 09/896,865

(22) Filed: Jun. 29, 2001

Related U.S. Application Data

(63) Continuation-in-part of application No. 09/819,887, filed on Mar. 28, 2001.

(51) Int. Cl.[7] .............................................. A23B 7/153
(52) U.S. Cl. ....................... 426/262; 426/271; 426/310; 426/335; 426/615
(58) Field of Search ................................ 426/615, 262, 426/541, 335, 532, 648, 102, 89, 321, 326, 329, 302, 271

(56) References Cited

U.S. PATENT DOCUMENTS

| | | | | | |
|---|---|---|---|---|---|
| 4,066,795 A | * | 1/1978 | Dave | ........................... | 426/259 |
| 4,557,937 A | * | 12/1985 | Bournier | ..................... | 426/241 |
| 5,919,507 A | * | 7/1999 | Beelman et al. | ............. | 426/268 |
| 5,925,395 A | * | 7/1999 | Chen | ........................... | 426/302 |
| 6,039,992 A | * | 3/2000 | Compadre et al. | ........... | 426/332 |
| 6,139,890 A | * | 10/2000 | Simpukas | .................... | 426/268 |
| 6,287,617 B1 | * | 9/2001 | Bender et al. | ............... | 426/335 |

* cited by examiner

*Primary Examiner*—Carolyn Paden
(74) *Attorney, Agent, or Firm*—Huntley & Associates

(57) ABSTRACT

Preservative compositions using GRAS (generally recognized as safe) ingredients are incorporated into a commercially viable three-stage preservation process for mushrooms. The process includes contacting the mushrooms with a high pH solution for microbial reduction; a neutralizing step to return the pH of the mushrooms to their about physiological pH; and an anti-browning step that incorporates suitable antioxidants and ancillary compounds to maintain the color of the finished product. Specifically disclosed is a method for preserving fresh mushrooms comprising the steps of exposing the mushrooms to a aqueous antimicrobial solution with a pH of 10.5–11.5; treating the mushrooms with a pH neutralizing buffer consisting of an organic acid and a salt of an organic acid and then subjecting the mushrooms to a combination of an anti-browning agent, a source of calcium and a chelating agent.

32 Claims, 2 Drawing Sheets

PRESERVATION COMPOSITIONS AND PROCESS FOR MUSHROOMS

CROSS-REFERENCE TO RELATED APPLICATION

This is a continuation-in-part of copending application Ser. No. 09/819,887, filed Mar. 28, 2001.

BACKGROUND OF THE INVENTION

Fresh-cut fruits and vegetables, with minimal processing and ready to eat, are the fastest growing segment of the produce market. Sulfite solutions were historically used to wash fruits, vegetables and mushrooms. Due to the detrimental effects of water and the undesirable effects of sulfites, minimally processed or ready to eat mushrooms with acceptable quality and shelf life for retail markets have not been achieved on a commercially viable basis.

Commercial production practices of growing mushrooms in straw-bedded horse manure compost covered with a fine layer of peat or other "casing material" yield harvested mushrooms with undesirable appearance and requires the consumer to wash the mushrooms prior to use. Mushrooms are typically harvested by hand leading to the introduction and spread of fluorescent Pseudomonads and other spoilage organisms that lead to accelerated decay and discoloration of the mushrooms.

Consumers identify whiteness and cleanliness of fresh mushrooms (Agaricus bisporus) as the main factors of quality. If an economical process could be developed to remove the casing material and compost from the surface of mushrooms while minimizing bacterial attack, the processors could create new markets and increase the sale of mushrooms. The consumer would prefer to purchase ready to use mushrooms that are free of such contaminants and have the opportunity to readily mix them with other food components. In the view of the grower/processor and end user, mushrooms would then join the category of minimally processed or fresh-cut produce and occupy the convenience section of the produce aisle.

The discoloration of mushrooms is due principally to enzymatic browning that is triggered when substrate and enzyme (tyrosinase or polyphenol oxidase) are allowed to mix. Tyrosinase, which occurs naturally at high levels in the cap cuticle or surface of the mushrooms, interacts with a number of phenolic substances that are also present in the cap. In healthy tissue, enzyme and substrate are segregated in separate subcellular compartments. Upon mechanical, bacteriological or physiological injury to the mushroom, enzyme and substrate are allowed to mix and subsequent discoloration occurs. Due to the fragile nature of mushrooms and susceptibility to attack by bacteria it would be highly desirable to develop a commercially viable protocol to minimize mechanical and bacterial damage to the mushroom tissue and thus indirectly inhibit enzymatic browning. It is further desirable to combine this with a preservation step that would directly inhibit enzymatic browning. It would be most efficient if such treatments could be a part of a washing process that would also remove undesirable particulate matter that clings to the mushroom cap surface after harvesting.

Traditionally, the surfaces of mushrooms have been washed with sulfite solutions to remove unwanted debris and bleach the mushrooms to a desired whiteness level. However, in 1986, the U.S. FDA banned the application of sulfite compounds on mushrooms due to allergic reactions experienced by asthmatic consumers when exposed to such compounds. Subsequent to the ban, numerous attempts have been made to identify alternative treatment compounds to sulfites. Although mushrooms treated with sulfite solutions exhibit a very desirable color at day 1 (post-treatment), there is little reduction in the surface microbial population. Hence, the beneficial effect of sulfite solutions on quality is short term. After only two to three days of refrigerated storage, bacterial decay of the sulfite treated mushrooms is evident. Growers accepted this trade off as sulfites are very cheap and the bleached appearance combined with the removal of undesirable debris yields an acceptable product for short periods of time. However, this short shelf life does not produce lasting results and is inadequate for retail distribution.

The banning of sulfite washes stimulated scientists to identify alternative systems and to extend the shelf life to meet the requirements for retail distribution. McConnell (1991) developed an aqueous preservative wash solution containing 10,000 ppm hydrogen peroxide and 1000 ppm calcium disodium EDTA. Hydrogen peroxide functions as a bactericide via oxidation injury to DNA and other cellular components. Ethylene diamine tetraacetic acid (EDTA) enhances the antimicrobial activity of hydrogen peroxide and reduces browning by sequestering copper, a cofactor required by tyrosinase. In 1994, Sapers modified McConnell's protocol into a two stage process that utilized 10,000 ppm hydrogen peroxide in stage 1 and a combination of sodium erythorbate, cysteine and EDTA in stage two. Although these protocols were an improvement over the sulfite treatments, they proved expensive.

High pH solutions are known to be effective as antimicrobial treatments for mushrooms. Catalano and Knabel (1994) determined that increasing a solution wash to pH 11.0 caused at least a 3-log 10 reduction in the number of viable Salmonella cells within one hour of inoculation. Higher pH levels are especially effective against gram-negative organisms such as Pseudomonas, the predominant genus on mushrooms (Aubrey). In 1999, Beelman and Duncan incorporated the use of a high pH wash with an antibrowning solution in a two-stage process (U.S. Pat. No. 5,919,507). The Beelman-Duncan process used a high pH first stage as the antimicrobial treatment and a second stage of sodium erythorbate, calcium and EDTA to minimize enzymatic browning. While this process combined and improved the teaching of McConnell and Sapers, it narrowly focused on a two-stage sequence with limited chemical selection in each process step. Specifically, the Beelman-Duncan process limited the pH neutralizing step to include solutions of erythorbic acid and sodium erythorbate. In addition, Beelman applied the erythorbic solution immediately after the antimicrobial contacting step. This restrictive sequence resulted in the rapid degradation of the sodium erythorbate solution in the neutralization stage and the need for increased quantities of the anti-browning materials. Consequently, the Beelman process did not address the variability in raw material and proved too expensive to be adopted by the processors and did not achieve commercial viability.

While the science of preservation of fresh mushrooms has advanced from the days of sulfite wash solutions, there remains a need for an efficient and economical method for treating mushrooms that removes compost and casing material, reduces microbial activity, minimizes enzymatic browning and thereby improves appearance and increases shelf life of fresh whole and sliced mushrooms.

SUMMARY OF THE INVENTION

The present invention provides sulfite alternative compositions and a method for preserving mushrooms that is cost effective and provides adequate shelf life for retail distribution of the product. The method comprises the steps of contacting the mushrooms with an anti-microbial solution; rinsing the mushrooms with a neutralizing buffer solution; and treating the mushrooms with a browning inhibitor and a chelating agent.

Specifically, the instant invention provides a method for preserving mushrooms comprising the steps of contacting the mushrooms with an antimicrobial solution having a pH from about 10.5 to about 11.5; rinsing the mushrooms at least once with at least one aqueous pH neutralizing solution comprising organic acid and at least one salt of an organic acid substantially free from erythorbic acid and sodium erythorbate; and contacting the mushrooms at least once with at least one solution comprising a browning inhibitor and a chelating agent.

The invention further provides a three stage process that includes calcium and EDTA to minimize enzymatic browning in the third stage.

DETAILED DESCRIPTION OF THE INVENTION

Figure 1:
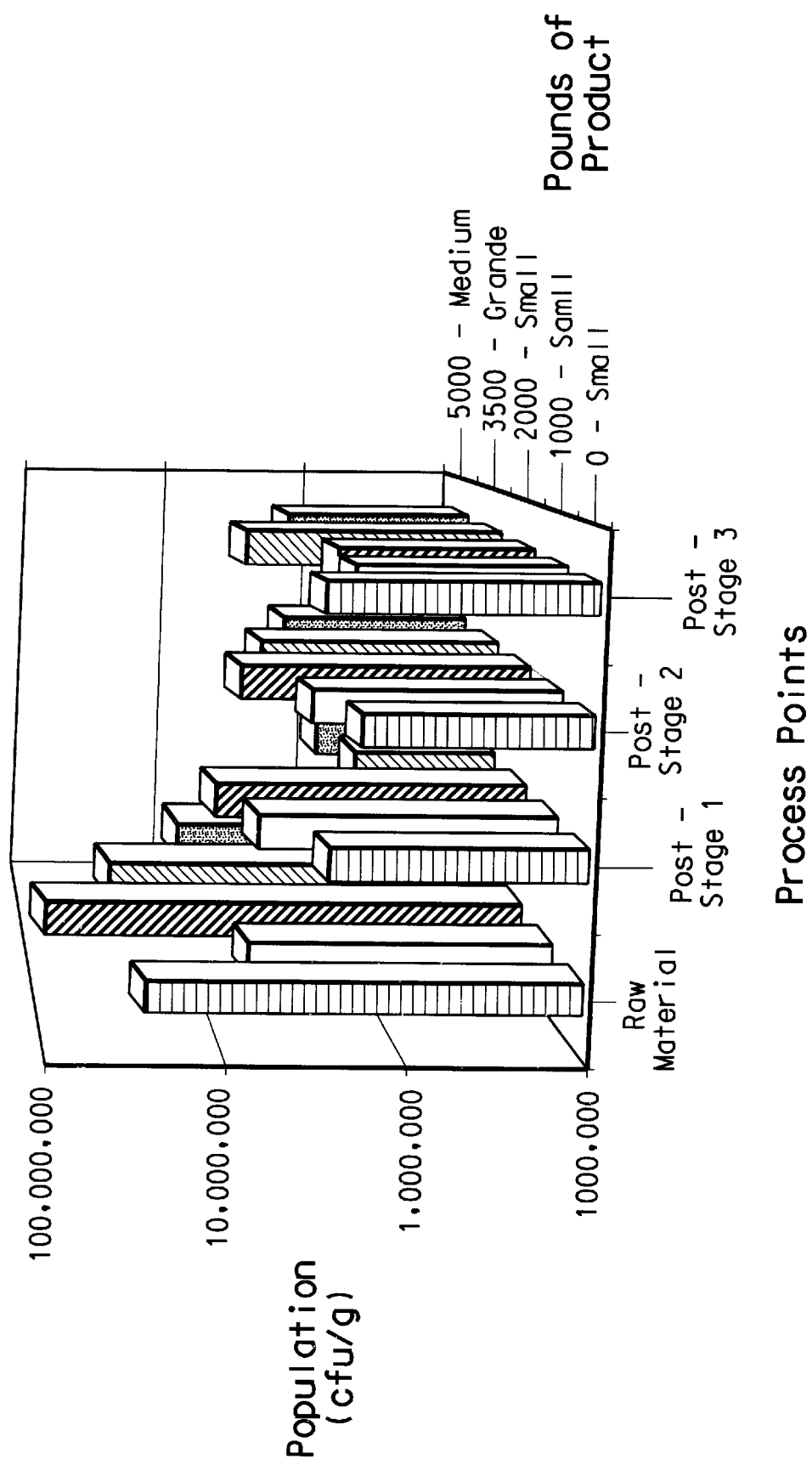
FIGS. 1 and 2 are graphical representations of test results realized using the three-stage process of the present invention.

The present invention is based on the discovery that a three stage preservation method for mushrooms provides improved efficiency and efficacy in cleaning and preserving mushrooms on a commercial scale.

The present invention uses a high pH solution as an anti-microbial treatment for fresh whole or sliced mushrooms. This significantly reduces the microbial load and reduces bacterial decay of the mushroom tissue and subsequent browning. However, the mushroom cap tissue is susceptible to damage by exposure to the high pH solution. Therefore, the present process includes a rapid neutralization following the high pH wash. The rapid neutralization minimizes tissue damage. The rapid neutralization is important to the quality of the finished product and the exposure time should be carefully controlled.

The present invention also includes an antibrowning step to deal with enzymatic browning. The antibrowning step incorporates a solution comprising antioxidant or browning inhibitor, and preferably calcium to maintain cellular tissue and to enhance browning inhibition. EDTA is also preferably used to further increase browning inhibition. By separating the neutralization step and the anti-browning step, the process is made cost effective due to the reduced depletion of the relatively expensive anti-browning solution. Thus, the present invention consists of three distinctly functional stages: a microbial stage, a neutralization stage and an anti-browning stage.

The first step of the instant process involves contacting the mushrooms with an anti-microbial buffer solution having a pH of from about 10.5 to about 11.5. A wide variety of compounds can be used in this solution to attain the desired pH, including, for example, sodium bicarbonate, sodium carbonate and sodium hydroxide. The buffering compounds can be used alone or in combination. Of these buffering compounds, the combination of sodium bicarbonate and sodium carbonate is preferred. About from 0.3 to 0.5% by weight sodium bicarbonate and about from 0.05 to 0.10% by weight of sodium bicarbonate has been found to be particularly satisfactory. In general, the initial contacting with the anti-microbial buffer solution is carried out for about from 20 to 40 seconds at ambient temperatures of about 25° C. Somewhat elevated temperatures can provide greater antimicrobial action, which permits lower dwell times in this solution.

The mushrooms are thereafter contacted with at least once with at least one aqueous pH neutralizing buffer solution comprising organic acid and at least one salt of an organic acid and substantially free from erythorbic acid and sodium erythorbate. This can be accomplished by applying the buffer solution by any convenient means, including, for example, by dipping, spraying and cascading. In general, this neutralizing solution has a pH of about from 3.0 to 5.0. The acids and bases used for the preparation of the salts are preferably weak acids and bases. Representative of the organic acids and salts of organic acids which can be used in the instant process include citric acid and sodium citrate, respectively. For example, a 0.1 N solution of citric acid, having a pH of about 3.5, can be used effectively. The combination of citric acid and sodium citrate is preferred, but other acids, salts, and combinations will be readily apparent to those skilled in the art. For example, other organic acids which can be used include malic, acetic, phosphoric, and lactic acids.

The rinsing step is carried out to reduce the pH of the mushrooms to substantially their natural pH. In this context, the rinsing is carried out with the aqueous buffer solution at a pH of about from 3.0 to 5.0. The contacting time will vary, for example, with the pH of the mushrooms after the anti-microbial solution treatment and the volume of rinsing solution, but is typically about from 10 to 30 seconds.

The third step of the process of the instant invention is treating the mushrooms at least once with at least one solution comprising a browning inhibitor and a chelating agent. A wide variety of browning inhibitors known in the art can be used, which retard the effect of tyrosinase. These are typically reducing agents, of which sodium erythorbate, erythorbic acid, ascorbic acid and calcium ascorbate are representative, and which are preferred. A similarly broad range of known chelating agents can be used, which have a high affinity for copper. These can include, for example, polyphosphates such as sodium hexametaphosphate, and others currently approved for use on fruits and vegetables, and categorized by the Food and Drug Administration as Generally Recognized As Safe (GRAS). Calcium disodium EDTA has been found to be particularly satisfactory, and is accordingly preferred.

The pH of individual solutions can be monitored for the purpose of maintaining the optimum pH and the concentration of sodium erythorbate monitored to maximize the inhibition of enzymatic browning of the mushrooms. In a preferred embodiment of the instant process, the solution used in the third treating step further comprises calcium chloride. The pH of individual solutions is monitored for the purpose of maintaining the optimum pH and the concentration of sodium erythorbate monitored to maximize the inhibition of enzymatic browning of the mushrooms.

Advantages of the present process over other multiple stage processes include the use of higher pH solutions in the first stage, resulting in improved microbial kill, a rapid neutralization step that minimizes tissue damage, less carry over and a reduction in the rate of depletion of the expensive anti-browning chemicals, better dirt removal, less solution uptake (high solution uptake causes the appearance of light grey disclororation, commonly referred to as "window paning"), reduced tank charging costs, reduced ingredient depletion and less foam in the final tank.

The instant process preferably comprises incorporating, into at least one treating step, at least one antifoaming composition. A wide variety of known defoaming or antifoaming compositions or surfactants can be used, of which silicon emulsions have been found to be particularly satisfactory, and are accordingly preferred. For maximum effectiveness, this component is preferably added to the first or second stages of the instant process. The specific quantity will depend on the surfactant selected and the volume of the treating baths, as can be readily determined by those skilled in the art.

The procedure can be and preferably is a continuous process whereby the mushrooms are introduced into a first tank and conveyed through each step with minimal mechanical damage. Extensive mechanical damage leads to excessive browning and depletion of active ingredients. Solutions of sodium bicarbonate and sodium carbonate are adjusted to the higher pH with sodium hydroxide to achieve the high pH state in the first stage and maintained at a temperature of at least about 25° C. In general, somewhat elevated temperatures improve the microbial kill. To avoid tissue damage, the exposure time is limited to about 20–40 seconds. After the antimicrobial step, the pH of the mushrooms is rapidly adjusted to approximately 6.5, which is more physiologically acceptable for the mushrooms. The rapid reduction in pH is accomplished during the second step in the process or the rinsing step. The rinsing occurs in a tank that contains a citrate buffer made from an organic acid and a salt of an organic acid and that is at ambient temperature. To minimize the uptake of solution, the mushrooms remain in stage two for only approximately 10–30 seconds. They are then transported by a conveyor that minimizes submersion depth, again to minimize uptake of solution, to the stage three (antibrowning) step. The antibrowning stage solution is maintained at ambient temperature and preferably comprises sodium erythorbate, calcium chloride, and EDTA as a treatment to minimize enzymatic browning. The mushrooms remain in this solution for approximately 20–40 seconds. The total immersion or solution exposure time during the three stage process is preferably limited to approximately 50–110 seconds.

When compared to other treatment protocols such a sodium metabisulfite or the Beelman-Duncan two stage process, mushrooms resulting from the process of the instant invention are superior in several ways. Although mushrooms treated with sulfites may initially have a better whiteness than mushrooms treated by the present invention, those resulting from the present invention exhibit a better appearance later in shelf life and exhibit a longer shelf life with acceptable color. There is a significant reduction in microbial load using this process whereas sulfites tend to exhibit little or no bactericidal effect. When compared to the Beelman-Duncan two stage process, mushrooms from the present three-stage process take up less solution, have a greater reduction in microbial load, and exhibit less enzymatic browning. The three distinct steps allow for the optimization of each functional component of the process and minimization of the depletion of active components in the anti-browning stage. This results in a significant reduction in cost of the process per pound of treated mushrooms.

The present invention is further illustrated in the following specific examples, using the materials, equipment and test procedures described.

Raw Material

Hybrid off-white mushrooms (*Agaricus bisporus*) were used for testing. Due to the inherent variability in commercially produced mushrooms all subsequent studies were conducted with similar mushrooms but grown and harvested under commercial production conditions in southeastern Pennsylvania. No grading was done beyond normal commercial protocols. Traditional horse-manure compost and conventional production practices were used. Mushrooms were generally harvested early in the day of processing. A composite of the harvest was used with the only differentiation being the harvest or flush as it is commonly referred to in the industry. As the teaching of this invention is a commercially viable process the use of average quality mushrooms was considered very important. First and second flush mushrooms, which account for the majority of mushrooms sold commercially were used for the pilot scale tests and within a given test either the first or second flush mushrooms were used. Harvested mushrooms were stored at 2–4° C. prior to processing. Experiments were conducted with whole and sliced mushrooms.

Treatment Solutions

Treatment solutions were generally made using available city or well water. However, the water was analyzed to determine the pH and any unusual concentration of specific elements.

Initial studies and early pilot scale tests compared the Beelman et al. two-stage process and the present three-stage process. All subsequent wash treatments where commercially grown mushrooms were used consisted of three distinct stages: the first stage is a high pH antimicrobial wash (typically 10.5–11.5 sodium bicarbonate, sodium carbonate buffer), the second stage is a neutralization step to return the mushrooms to the physiologically normal pH as quickly as possible, the third stage is a preservative step (typically a mixture of sodium erythorbate, calcium chloride, and EDTA). It is extremely important to neutralize the high pH solution quickly to avoid tissue damage and subsequent accelerated enzymatic browning and microbial growth.

Stage one (reported in Table 1) uses a combination of 0.04M sodium carbonate and 0.01M sodium bicarbonate adjusted to pH 11.2 with 10N sodium hydroxide. A surfactant is added to avoid frothing in the treatment tank and subsequent carry over to tank two. The temperature of the solution is maintained at 25° C.

Stage two neutralization solution is a 0.05M citrate buffer of citric acid and sodium citrate to achieve a pH range of 2.5–4.0 with a pH of 3.6 being the target. The temperature of this solution is ambient.

Stage three anti-browning step consisted of sodium erythorbate (2.0–3.0% by weight), calcium disodium EDTA (0.1% by weight) and anhydrous calcium chloride (0.1–0.2% by weight). The temperature of stage 3 is ambient.

The pH of individual solutions is monitored for the purpose of maintaining the optimum pH and the concentration of sodium erythorbate monitored to maximize the inhibition of enzymatic browning of the mushrooms.

Wash Process

Three commercial size tanks (FIG. 1) were filled with solution prepared with plant water. The temperature of tank 1 is maintained at 25° C. while the temperature of tank 2 and tank 3 equilibrated to ambient conditions. Chemical solutions and conditions used in the individual tanks are summarized in table 1. The single stage process is the current practice of using sulfite solutions to bleach and maintain the mushrooms. The two-stage process is the process developed by Beelman and Duncan.

Mushrooms are dumped gently into Tank 1 and moved gently through the tank at the designated rate via paddles. The process line is a continuous process with tank-to-tank transition as gentle as possible and with minimal submersion to minimize solution uptake and damage to the mushrooms. Excess moisture was drained during the transition from Tank 1 to Tank 2, which helped to minimize carryover into Tank 2.

Quality Measurements

Effectiveness of the individual treatments at maintaining whiteness and inhibiting post-processing browning was determined by measuring mushroom cap color on designated days of storage. Color was measured at three locations on the surface of each mushroom cap using either human observation or a tristimulus colorimeter. The colorimeter was calibrated using a standard plate supplied with the instrument and L* a*b color coordinates were used for all measurements. A target color of L=97.00, a=2.00, and b=0.00 was used as a reference standard for internal calculation of overall color deviation (Delta E) from that of the "ideal white mushroom" (Solomon, 1991).

In most studies, cap (visual), stem color and maturity were rated on a 1 to 5 scale with 1 being the best. Notations were made for aroma and extent of visible microbial degradation.

TABLE 1

| | Single-Stage Process | Two-Stage Process | Three Stage Process |
|---|---|---|---|
| Tank 1 | Water Sodium Metabisulfite Ambient temperature | Water Sodium bicarbonate pH 9.5–11.0 30–60 sec 10–25 C. | Water Sodium bicarbonate Sodium carbonate Sodium hydroxide surfactant pH 10.5–11.5 30 sec 25 C. |
| Tank 2 | None | Water Erythorbic acid Sodium erythorbate Calcium disodium EDTA Anhydrous Calcium Chloride pH 4.8 60–120 sec exposure | Water Citric acid Sodium citrate pH 3.0–5.0 15 sec Surfactant |
| Tank 3 | None | None | Water Sodium erythorbate Calcium disodium EDTA Anhydrous calcium chloride Surfactant pH 7.5 35 sec dwell time |

EXAMPLE 1

Reducing uptake of solution and minimizing depletion of the preservative solution in tank 3.

Treatment solutions were prepared with deionized water. Stage 1 was maintained at 25° C. for multiple stage wash procedures while the sulfite control was at ambient temperature. The objective was to identify a process that would meet the economic targets of the processor and yield results (quality and shelf life) as good or better than the two-stage process reported by Beelman and Duncan. The mushrooms were held at 10° C. Three-stage processes (treatments 5,7, 9) yielded results as good as or better then the best 2-stage process with regard to overall quality and shelf life. Treatment 7 was the best with regard to appearance due in part to the reduced exposure time and less uptake of solution.

TABLE II

| Treatment | Description | Color of Stored Mushroom (L* values) | | |
|---|---|---|---|---|
| | | Day 0 | Day 3 | Day 6 |
| 1 | Sodium bicarbonate buffer at pH 10.5 (30 sec); 3% erythorbic acid/sodium erythorbate + 1000 ppm EDTA + 1000 ppm calcium chloride (60 sec) | 94.14 | 94.24 | 94.03 |
| 2 | Sodium bicarbonate buffer at pH 10.5 (30 sec); 0.05M citrate buffer @ pH 3.4 (15 sec); 1.0% sodium erythorbate + 1000 ppm EDTA + 1000 ppm calcium chloride (15 sec) | 94.54 | 93.45 | 90.06 |
| 3 | Sodium bicarbonate buffer at pH 10.5 (30 sec); 0.05M citrate buffer @ pH 4.6 (15 sec); 1.0% sodium erythorbate + 1000 ppm EDTA + 1000 ppm calcium chloride (15 sec) | 92.97 | 89.84 | 83.05 |
| 4 | Sodium bicarbonate buffer at pH 10.5 (30 sec); 0.05 citrate buffer at pH 3.4 (15 sec); 1.5% sodium erythorbate + 1000 ppm EDTA + 1000 ppm calcium chloride (15 sec) | 94.53 | 94.22 | 91.66 |
| 5 | Sodium bicarbonate buffer at pH 10.5 (30 sec); 0.05M citrate buffer at pH 4.6 (15 sec); 1.5% sodium erythorbate + 1000 ppm EDTA + 1000 ppm calcium chloride (15 sec) | 94.12 | 93.38 | 93.45 |
| 6 | Sodium bicarbonate buffer at pH 10.5 (30 sec); 0.05M citrate buffer at pH 3.4 (15 sec); 2.0% sodium erythorbate + 1000 ppm EDTA + 1000 ppm calcium chloride (15 sec) | 94.56 | 91.45 | 89.78 |
| 7 | Sodium bicarbonate buffer at pH 10.5 (30 sec); 0.05M citrate buffer at pH 4.6 (15 sec); 2.0% sodium erythorbate + 1000 ppm EDTA + 1000 ppm calcium chloride (15 sec) | 94.31 | 94.76 | 93.82 |
| 8 | Same as treatment 5 but with EDTA in the second (citrate) wash instead of in the third (erythorbate) wash. | 92.71 | 93.34 | 88.93 |
| 9 | Same as treatment 5, but with the citrate and sodium erythorbate washes at 30 sec each instead of 15 sec for a total exposure time of 90 sec. | 93.42 | 93.28 | 93.96 |
| 10 | Sodium bicarbonate buffer at pH 10.5 (30 sec); 0.05M citrate buffer at pH 3.4 (15 sec); 3.0% sodium erythorbate + 1000 ppm EDTA + 1000 ppm calcium chloride (15 sec) | 93.98 | 93.40 | 92.90 |

EXAMPLE 1, CONTINUED

Effect of washing on quality parameters of mushrooms. Day 6. (1=best, 5=worst)

| Treatment | Description | Cap Color | Stem Color | Aroma | Maturity | Microbial |
|---|---|---|---|---|---|---|
| 1 Control | Sodium bicarbonate buffer at pH 10.5 (30 sec); 3% erythorbic acid/sodium erythorbate + 1000 ppm EDTA + 1000 ppm calcium chloride (60 sec) | 1 | 1 | | 3 | |

-continued

| Treatment | Description | Cap Color | Stem Color | Aroma | Maturity | Microbial |
|---|---|---|---|---|---|---|
| 2 | Sodium bicarbonate buffer at pH 10.5 (30 sec); 0.05 M citrate buffer @ pH 3.4 (15 sec); 1.0% sodium erythorbate + 1000 ppm EDTA + 1000 ppm calcium chloride (15 sec) | 2 | 2 dark | Fishy | 2 | Bacterial blotch |
| 3 | Sodium bicarbonate buffer at pH 10.5 (30 sec); 0.05 M citrate buffer @ pH 4.6 (15 sec); 1.0% sodium erythorbate + 1000 ppm EDTA + 1000 ppm calcium chloride (15 sec) | 4 dark edges | 3 brown | Sl. Fishy | 3 | Severe blotch |
| 4 | Sodium bicarbonate buffer at pH 10.5 (30 sec); 0.05 citrate buffer at pH 3.4 (15 sec); 1.5% sodium erythorbate + 1000 ppm EDTA + 1000 ppm calcium chloride (15 sec) | 2 | 1 | Sl. Ammonia | 3 | blotch |
| 5 | Sodium bicarbonate buffer at pH 10.5 (30 sec); 0.05 M citrate buffer at pH 4.6 (15 sec); 1.5% sodium erythorbate + 1000 ppm EDTA + 1000 ppm calcium chloride (15 sec) | 2 | 2 | | 3 | |
| 6 | Sodium bicarbonate buffer at pH 10.5 (30 sec); 0.05 M citrate buffer at pH 3.4 (15 sec); 2.0% sodium erythorbate + 1000 ppm EDTA + 1000 ppm calcium chloride (15 sec) | 3 sl. darkening | 3 browning | Fishy | 4 | Severe blotch |
| 7 | Sodium bicarbonate buffer at pH 10.5 (30 sec); 0.05 M citrate buffer at pH 4.6 (15 sec); 2.0% sodium erythorbate + 1000 ppm EDTA + 1000 ppm calcium chloride (15 sec) | 1 | 1 | | 2 | |
| 8 | Same as treatment 5 but with EDTA in the second (citrate) wash instead of in the third (erythorbate) wash. | 2.5 sl. Yellow | 1.5 | Fishy | 3 | blotch |
| 9 | Same as treatment 5, but with the citrate and sodium erythorbate washes at 30 sec each instead of 15 sec for a total exposure time of 90 sec. | 2 | 2 | | 3 | blotch |
| 10 | Sodium bicarbonate buffer at pH 10.5 (30 sec); 0.05 M citrate buffer at pH 3.4 (15 sec); 3.0% sodium erythorbate + 1000 ppm EDTA + 1000 ppm calcium chloride (15 sec) | 2 | 1.5 darkening | Fishy | 4 | Some Blotch |

EXAMPLE 2

The 3-stage process (treatment 7) yielded mushrooms of equal or better quality than the standard 2-stage process as illustrated by L*-values (whiteness readings). The reduced exposure time also limited solution uptake, which is detrimental to quality and shelf life.

| Treatment | Description | Storage Color (L* values) | | |
|---|---|---|---|---|
| | | Day 0 | Day 3 | Day 6 |
| 1 | Sodium sulfite-Control | 91.48 | 90.09 | 87.28 |
| 2 Two-Stage Control | Sodium bicarbonate buffer at pH 10.5 (30 sec); 3.0% erythorbic acid/sodium erythorbate + 1000 ppm EDTA + 1000 ppm calcium chloride (60 sec) | 93.18 | 92.72 | 92.44 |
| 3 | Sodium bicarbonate buffer at pH 10.5 (30 sec); dip mushrooms in 0.05M citrate buffer at pH 3.5 (5 sec); 3% sodium erythorbate + 1000 ppm EDTA + 1000 ppm calcium chloride (15 sec) | 92.72 | 90.94 | 90.25 |
| 4 | Same as treatment 3, but with a 5 sec water rinse at end | 89.76 | 90.31 | 89.08 |
| 5 | Same as treatment 3, but with 1.5% sodium erythorbate instead of 3.0% | 91.68 | 90.89 | 89.73 |
| 6 | Same as treatment 5, but with a 5 sec water rinse at the end | 89.49 | 88.55 | 89.03 |
| 7 | Same as treatment 3, but with a | 93.87 | 93.02 | 92.49 |

-continued

| Treat-ment | Description | Storage Color (L* values) | | |
|---|---|---|---|---|
| | | Day 0 | Day 3 | Day 6 |
| | retention time of 30 sec in sodium erythorbate solution, instead of 15 sec | | | |
| 8 | Same as treatment 7, but with a 5 sec water rinse at the end | 91.14 | 92.23 | 90.75 |

EXAMPLE 3

Three-stage treatment illustrating equal or superior performance with reduced exposure times and reduced concentration of erythorbate resulting in an acceptable processing cost. Three-stage treatments 2, 3, 5 and 6 all outperformed the two-stage process over the duration of the shelf life period as illustrated by the higher L* value readings. The advantage of the 3-stage process is at day 6 when the retail consumer typically sees the product.

| | Treatment and Description | Day 0 | Day 3 | Day 6 |
|---|---|---|---|---|
| 1 | Sodium bicarbonate buffer at pH 10.5 (30 sec); 3% erythorbic acid/sodium erythorbate + 1000 ppm EDTA + 1000 ppm calcium chloride (60 sec) (standard 2-stage process) | 94.31 | 93.82 | 91.83 |
| 2 | Sodium bicarbonate buffer at pH 10.5 (30 sec); 0.05 citrate buffer at pH 3.4 (15 sec); 1.0% erythorbate + 1000 ppm EDTA + 1000 ppm calcium chloride (15 sec) | 93.67 | 92.31 | 92.72 |
| 3 | Sodium bicarbonate buffer at pH 10.5 (30 sec); 0.05M citrate buffer at pH 4.6 (15 sec); 1.0% erythorbate + 1000 ppm EDTA + 1000 ppm calcium chloride (15 sec) | 94.13 | 93.30 | 92.93 |
| 4 | Sodium bicarbonate buffer at pH 10.5 (30 sec); 0.05M citrate buffer at pH 3.4 (15 sec); 1.5% erythorbate + 1000 ppm EDTA + 1000 ppm calcium chloride (15 sec) | 93.43 | 93.95 | 90.93 |
| 5 | Sodium bicarbonate buffer at pH 10.5 (30 sec); 0.05M citrate buffer at pH 4.6 (15 sec); 1.5% erythorbate + 1000 ppm EDTA + 1000 ppm calcium chloride (15 sec) | 93.79 | 93.18 | 93.26 |
| 6 | Sodium bicarbonate buffer at pH 10.5 (30 sec); 0.05M citrate buffer at pH 3.4 (15 sec); 2.0% erythorbate + 1000 ppm EDTA + 1000 ppm calcium chloride (15 sec) | 94.36 | 93.20 | 93.49 |
| 7 | Sodium bicarbonate buffer at pH 10.5 (30 sec); 0.05M citrate buffer at pH 4.6 (15 sec); 2.0% erythorbate + 1000 ppm EDTA + 1000 ppm calcium chloride (15 sec) | 93.12 | 92.70 | 90.86 |
| 8 | Same as 4 but with EDTA in second (citrate) tank instead of the third (erythorbate) tank. | 93.12 | 92.40 | 92.14 |

EXAMPLE 4

Comparison of the Beelman-Duncan process and the present three-stage process using mushrooms grown under conventional production protocols and washed using a commercial processing line.

First-flush mushrooms were treated with several variations of the three-stage process as well as the standard two-stage process of Beelman and Duncan. The control was commercially produced sulfite-washed mushrooms. Tank 1 was 0.424% sodium carbonate, 0.084% sodium bicarbonate buffer (0.05M), pH=10.5, temperature 25° C.; tank 2 was 0.49% citric acid, 0.72% sodium citrate buffer, pH 4.5, temperature 14° C.; tank 3 was 3.0% sodium erythorbate (monohydrate), 1000 ppm calcium disodium EDTA, 1000 ppm calcium chloride (dihydrate), pH 7.2–7.4. After washing, the mushrooms were placed in cold storage prior to vacuum cooling. Mushrooms were vacuum cooled for 18 min to an internal temperature of 2–3° C. Mushrooms were packaged in commercial 10-LB ventilated corrugated containers. Mushrooms treated with the various three-stage treatments retained shelf life quality as well as those treated with the commercial sulfite solution. There were no major differences across the different three-stage treatments and the mushrooms exhibited an additional 2–3 days of salable quality. The three-stage treatments were superior to the standard two-stage process. Overall ranking scale (1=best) was used to compare the processes.

The fact that the 3-stage process worked as well with regard to appearance as the commercial sulfite wash (banned by FDA) and provided additional shelf life indicated that this process performs adequately for commercial use. Results are especially significant in that the starting raw material was first-flush mushrooms, which are generally of lower quality than second flush mushrooms.

Evaluation of mushrooms processed and stored under commercial conditions for 3 days at 2–4° C. The plant manager performed evaluations. An overall ranking scale (1=best) was used to compare the processes.

| Treatment | Cap Color | Stem End Color | Overall Salability | Comments | Overall Ranking |
|---|---|---|---|---|---|
| 3-stage # 1 30s/15s/15s | Better than sulfite control | Equal to or better than sulfite control | Salable | Good throughout | 1 |
| 3-stage # 2 30s/30s/15s | Some blotch starting, but no different from sulfite control | Equal to sulfite control | Salable | Some dimpling and blotch | 4 |
| 3-stage # 3 30s/15s/30 | A little better than sulfite control | Equal to sulfite control | Salable | | 2 |
| 3-stage # 4 30s/30s/30s | A little better than sulfite control | Not as good as sulfite control | Salable | | 3 |
| 3-stage # 5 30s/30s/30s with rinse | Caps dirty, equal to control | Equal to sulfite control | Salable | | 4 |
| 2-stage # 6 | More blotch than sulfite control, not as good | Equal to sulfite control | Marginal | A lot of blotch | 5 |
| Sulfite Control | Acceptable | Acceptable | Salable | | 4 |

EXAMPLE 5

First and second flush, calcium chloride-irrigated mushrooms were washed in the standard 3-stage process, a modified 2-stage process in which the second and third steps were combined and a bucket test to evaluate the significance of the mechanical damage. Mushrooms washed in the bucket test of the 3-stage process were rated "excellent" and almost as good as sulfite-washed mushrooms. Those washed with the standard 3-stage process were rated "good" by day 2 and were still acceptable to marginal by day 6, but were not as bright as those from the bucket test. However, mushrooms treated via the 3-stage process were considerably brighter than mushrooms washed with the 2-stage process, thus confirming the need to separate the functionalities of the ingredients in separate tanks Standard 3-stage process:

Stage 1—40 sec (target is 30 sec) in 0.424% sodium carbonate, 0.084% sodium bicarbonate at approx. 25° C., pH 10.5

Stage 2—45 sec (target time 15 sec) in 0.49% citric acid, 0.72% sodium citrate at approx 16° C., pH 4.6.

Stage 3—16 sec (target time 15 sec) in 3.0% sodium erythorbate, 0.1% calcium disodium EDTA, 0.1 % calcium chloride at approx. 16° C., pH 7.3

Post-treatment rinse—1 oz/LB

Modified 2-stage process

To further confirm the importance of separating the functional steps of the wash process a modified 2-stage process was tested where steps 2 and 3 of the 3-stage process were combined.

Stage 1—45 sec (target time 30–45 sec) in 0.424% sodium carbonate, 0.084% sodium bicarbonate at approx 25° C., pH 10.5.

Stage 2—16 sec (target time 15 sec) in 3.0% sodium erythorbate, 0.1 % calcium chloride, 0.1 % calcium disodium EDTA, and adjusted to pH 4.8 with citric acid Post-treatment rinse—1 oz/LB

| | |
|---|---|
| 2-Stage Process (Steps 2 and 3 of three-stage process combined) | Product rated acceptable to marginal. Not as bright as mushrooms from the 3-stage process, significantly more browning |
| 3-Stage Process | Product rated acceptable to marginal. Caps mostly white with only a few marks; stem ends had good color |
| 3-stage bucket test | Mushrooms from 2nd flush about as good as those from the 3-stage process (above), but those from the 1st flush were unacceptable due to lots of deep brown marks; probably due to over drying |

EXAMPLE 6

A three-stage process using sprays for stage 2 and stage 3 rather than submersion.

Mushrooms of four different quality levels were washed using the three-stage process but with the substitution of sprays for tank 2 and tank 3. Finished product was stored at 35° F. and compared with unwashed controls and sulfite-washed mushrooms.

Mushroom Quality (starting raw material)

Group 1: Second break, medium-size mushrooms (best quality of the four groups), picked and washed the same day.

Group 2: Second break medium-size mushrooms picked same day, in ½-LB tills, vacuum cooled (second best quality)

Group 3: California first break medium-size mushrooms picked the previous day, in lugs, vacuum-cooled (worst quality of the four categories)

Group 4: First break medium-size mushrooms picked same-day, in lugs, not vacuum-cooled.

Parameters for trial

Stage 1—15–30 sec at 25° C. in 0.424% sodium carbonate, 0.084% sodium bicarbonate (pH 10.4)

Stage 2—20 sec at 13° C. in 0.72% sodium citrate, 0.49% citric acid

Stage 3—10 sec at 13° C. in 3.5% sodium erythorbate, 0.2% calcium chloride and 0.1% calcium disodium EDTA The mushrooms were evaluated by technical personnel from a commercial mushroom processor.

Mushrooms were kept at room temperature for approximately 30 min after washing, then placed in the 35° F. cooler. Lugs were stacked and uncovered. Control (unwashed and sulfated mushrooms) was placed next to the treated material.

Results at Day 3

Group 1—Washed product looked good, caps were white on top, slightly gray around sides. Slightly better than sulfite-washed same day; sulfite-washed were slightly yellow. Stem ends ok, slight to moderate brown.

Group 2—3-stage wash product looked good, some bruising, otherwise as good as group 1.

Group 3—3-stage process looked marginal as they did on day 0. Acceptable for slicing.

Group 4—3-stage process looked acceptable to marginal, lot of bruising, overall not as bright as groups 1 and 2.

Although there was considerable mechanical damage the 3-stage processed mushrooms were acceptable and considered better then the sulfited control.

Day 5

The 3—stage processed mushrooms still looked good with little difference from day 3. The treated produce was slightly better than the unwashed controls and significantly better than the sulfite-washed product, which continued to yellow.

Day 7

Treated product still looked good. The 3-stage washed product clearly looked better than the unwashed controls and much better than the sulfite-washed mushrooms. There was some blotch on the unwashed controls but none on the washed mushrooms.

EXAMPLE 7

Three-stage Treatment Trial Substituting Spray Application for Submersion in stages 2 and 3

Treatments were the same as in Example 6.

This was a similar trial to that described in Example 5 but with lesser quality starting raw material. Mushrooms were dumped onto a metal grill (slopes to tank 1) to remove debris. The mushrooms remained in the barrel washer for 15–30 seconds. Stage 2 consisted of spray nozzles mounted over a conveyor and supplied by a 50-gal tank. Total time for stage 2 was 20 sec. Stage 3 also consisted of spray nozzles over a second conveyor and fed by a 50-gal tank. The mushrooms were allowed to drain and were sorted for defects and size.

In general the results were not as good due to the inferior quality of the starting raw material. None of the mushrooms in this trial were of superior quality and some were clearly marginal quality at the time of washing. Three of the six tested groups were harvested the day before.

Day 7 Results pallet 1 (large, second break, harvested day before washing, decent quality prior to washing)

Sliced—excellent quality (rated 8-9 on scale of 1 to 10, 10 being best)

Whole—good quality—biggest problem was brown spots due to mechanical damage (rated 7)

Pallet 2 (mediums, second break, harvested day before washing, fair quality prior to washing)

Sliced—excellent quality (rated 9)

Whole—good quality—biggest problem was brown spots due to mechanical damage (rated 7)

Unwashed Controls—were brown overall (rated 3)

Pallet 3 (mediums, first break, harvested day before washing, low quality prior to washing)
  Sliced—good quality (rated 7 on a scale of 1 to 10)
  Whole—decent quality (rated 6 on a scale of 1 to 10)
  Unwashed controls—somewhat brown overall (rated 4)

Pallet 4 (medium size, first break, picked day of wash, decent quality prior to washing)
  Sliced—very good quality (rated 8)
  Whole—good quality—browning where there was mechanical damage (rated 7)
  Unwashed controls—a little brown overall (rated 5)

Pallet 5 (buttons, picked day of wash, low quality prior to washing)
  Whole—marginal quality (rated 5)

Pallet 6 (mediums, first break, picked day of washing, good quality prior to washing)
  Sliced—marginal—unacceptable quality, a lot of graying (rated 4
  Whole—decent quality (rated 6)

EXAMPLE 8

Effect of Three-stage Process on Depletion of Active Ingredients

The largest cost factor in the two-stage process is erythorbate, added as sodium erythorbate and erythorbic acid. The largest cost factor in the three-stage process is sodium erythorbate. The concentration of erythorbate must be maintained between approximately 2 and 3% in order to effectively preserve the appearance of the washed mushrooms. Therefore, the depletion and maintenance of erythorbate is a critical component in both efficacy and the economics of both wash processes.

Mushrooms were washed in separate commercial trials of the two-stage and three-stage processes. The changes in concentration of erythorbate were monitored in tank 2 of the two-stage process and tank 3 of the three stage process. Maintenance of erythorbate was calculated based on measured erythorbate concentration and tank volume.

The conditions for the two-stage process were as follows: Stage one tank conditions were 400 gallons at 0.43% sodium bicarbonate, 0.18% sodium hydroxide, pH 10.4, 24.2° C., 23 sec dwell time. Stage two tank conditions were 550 gallons at 2.4% sodium erythorbate, 0.6% erythorbic acid, 0.1% calcium chloride, 0.1% EDTA, pH 4.7, 15.8° C., 60 sec dwell time.

The conditions for the three-stage process were as follows: Stage one tank conditions were 400 gallons at 0.43% sodium carbonate, 0.084% sodium bicarbonate, pH 10.4, 21.7° C., 30 sec dwell time. Stage two tank conditions were 550 gallons at 0.49% citric acid, 0.72% sodium citrate, pH 4.5, 18° C., 35 sec dwell time. Stage three tank conditions were 190 gallons at 3% sodium erythorbate, 0.1 % calcium chloride, 0.1 % EDTA, 15 sec dwell time.

The depletion of erythorbate is two to three times greater for the two-stage process compared to the three-stage process. Approximately three times the weight of mushrooms can be processed per LB of sodium erythorbate using the three-stage process compared to the two-stage process.

| | Two-Stage Process | |
|---|---|---|
| Mushrooms Processed (lbs) | Measured Tank 2 (550 gal) Erythorbate Concentration (%) | Weight erythorbate added (sodium erythorbate plus erythorbic acid) (lbs) |
| 100 | 3.0 | 137.6 initial |
| 1700 | 2.7 | |
| 3000 | 2.5 | |
| 5000 | 2.2 | |
| 7000 | 1.9 | |

Calculation of erythorbate used: 137.6 − ((137.6) (1.9/3.0)) = 50.5 lbs.
Calculation of erythorbate used per lb mushroom processed: 50.5 lbs/7000 lbs = 0.0072 lbs erythorbate per lb mushroom processed.
LBS of mushrooms/LB of sodium erythorbate: 7,000/50.5 = 138.6

| | Three-Stage Process | |
|---|---|---|
| Mushrooms Processed (lbs) | Measured Tank 3 (190 gal) Erythorbate Concentration (%) | Weight sodium erythorbate added (lbs) (to keep concentration > 2%) |
| 0 | 2.9 | 47.5 initial |
| 1329 | 2.7 | |
| 2450 | 2.6 | |
| 3244 | 2.3 | |
| 3939 | 2.1 | |
| 5246 | 3.1 | 13.1 |
| 6593 | 2.9 | |
| 7801 | 2.5 | |
| 9048 | 2.4 | |
| 10309 | 2.3 | |
| 11498 | 2.0 | |

Calculation of erythorbate used: 60.6 − ((47.5)(2.0/2.9)) = 28.4
Calculation of erythorbate used per lb mushroom processed: 28.4 lbs/111498 lbs = 0.0025 lbs erythorbate per lb mushroom processed.
LBS of mushrooms processed per LB of sodium erythorbate: 11498/28.4 = 404.9 LBS.

EXAMPLE 9

Two-Stage vs. Three-Stage Process: Effect on Cost of Charging Commercial Scale Mushroom Wash Line The costs of filling commercial sized tanks for the two-stage process were compared to the three stage process. Costs are represented as indexed costs with the cost of calcium disodium EDTA arbitrarily set at 100. Cost of the other individual ingredients is relative to EDTA.

The conditions for the two-stage process were as follows: Stage one tank conditions were 400 gallons at 0.43% sodium bicarbonate, 0. 18% sodium hydroxide, pH 10.4, 24.2° C., 23 sec dwell time. Stage two tank conditions were 550 gallons at 2.4% sodium erythorbate, 0.6% erythorbic acid, 0.1% calcium chloride, 0. 1% EDTA, pH 4.7, 15.8° C., 60 sec dwell time.

The conditions for the three-stage process were as follows: Stage one tank conditions were 400 gallons at 0.43% sodium carbonate, 0.084% sodium bicarbonate, pH 10.4, 21.7° C., 30 sec dwell time. Stage two tank conditions were 550 gallons at 0.49% citric acid, 0.72% sodium citrate, pH 4.5, 18° C., 35 sec dwell time. Stage three tank conditions were 190 gallons at 3% sodium erythorbate, 0.1% calcium chloride, 0. 1% EDTA, 15 sec dwell time.

The addition of a third treatment tank, and separation of the neutralization and browning inhibitor treatments as practiced in the three-stage process, results in significantly lower costs to charge commercial size treatment tanks as shown in the analysis below. The initial cost to fill the three tanks in the three-stage process is 60% less than the cost to fill the two tanks in the two-stage process.

Two-Stage Process

| | Stage One Tank 400 gallons | | |
|---|---|---|---|
| Ingredient | Initial Charge (lbs) | Indexed Ingredient Cost (IC/lb)[1] | Indexed Cost Initial Charge (IC)[2] |
| sodium bicarbonate | 14.14 | 16.87 | 238.54 |
| Total | | | 238.54 |

[1]Indexed Ingredient Cost (IC/lb): The actual 1998 ingredient costs per pound were divided by the actual 1998 cost of calcium disodium EDTA per pound and multiplied by 100.
[2]Indexed Cost Initial Charge (IC): (IC/lb) × Initial Charge (lbs)

| | Stage Two Tank 550 gallons | | |
|---|---|---|---|
| Ingredient | Initial Charge (lbs) | Indexed Ingredient Cost (IC/lb)[1] | Indexed Cost Initial Charge (IC)[2] |
| sodium erythorbate | 110.1 | 60.24 | 6632.42 |
| erythorbic acid | 27.5 | 141.45 | 3889.88 |
| calcium disodium EDTA | 4.6 | 100 | 460.00 |
| calcium chloride | 4.6 | 21.45 | 98.67 |
| Total | | | 11080.97 |

[1]Indexed Ingredient Cost (IC/lb): The actual 1998 ingredient costs per pound were divided by the actual 1998 cost of calcium disodium EDTA per pound and multiplied by 100.
[2]Indexed Cost Initial Charge (IC): (IC/lb) × Initial Charge (lbs)

Total indexed cost for charging tanks for two-stage process: 11319.51

Three-Stage Process

| | Stage One Tank 400 gallons | | |
|---|---|---|---|
| Ingredient | Initial Charge (lbs) | Indexed Ingredient Cost (IC/lb)[1] | Indexed Cost Initial Charge (IC)[2] |
| sodium carbonate | 14.14 | 16.87 | 238.54 |
| sodium bicarbonate | 2.80 | 10.12 | 28.34 |
| Total | | | 266.88 |

[1]Indexed Ingredient Cost (IC/lb): The actual 1998 ingredient costs per pound were divided by the actual 1998 cost of calcium disodium EDTA per pound and multiplied by 100.
[2]Indexed Cost Initial Charge (IC): (IC/lb) × Initial Charge (lbs)

| | Stage Two Tank 550 gallons | | |
|---|---|---|---|
| Ingredient | Initial Charge (lbs) | Indexed Ingredient Cost (IC/lb)[1] | Indexed Cost Initial Charge (IC)[2] |
| citric acid | 22.40 | 17.35 | 388.64 |
| sodium citrate | 32.94 | 26.02 | 857.10 |
| Total | | | 1245.74 |

[1]Indexed Ingredient Cost (IC/lb): The actual 1998 ingredient costs per pound were divided by the actual 1998 cost of calcium disodium EDTA per pound and multiplied by 100.
[2]Indexed Cost Initial Charge (IC): (IC/lb) × Initial Charge (lbs)

| | Stage Three Tank 190 gallons | | |
|---|---|---|---|
| Ingredient | Initial Charge (lbs) | Indexed Ingredient Cost (IC/lb)[1] | Indexed Cost Initial Charge (IC)[2] |
| sodium erythorbate | 47.50 | 60.24 | 2861.4 |
| calcium chloride | 1.6 | 21.45 | 34.32 |
| calcium disodium EDTA | 1.6 | 100 | 160.00 |
| Total | | | 3055.72 |

[1]Indexed Ingredient Cost (IC/lb): The actual 1998 ingredient costs per pound were divided by the actual 1998 cost of calcium disodium EDTA per pound and multiplied by 100.
[2]Indexed Cost Initial Charge (IC): (IC/lb) × Initial Charge (lbs)

Total indexed cost for charging tanks: 4568.34

EXAMPLE 10

Reduction of microbial populations on mushrooms washed by the three-stage process.

Mushrooms were washed in a commercial trial with the three-stage process. The conditions for the three-stage process were as follows: Stage one tank conditions were 0.43% sodium carbonate, 0.084% sodium bicarbonate, pH 11.1, 25.0° C., 30 sec dwell time. Stage two tank conditions were 0.49% citric acid, 0.72% sodium citrate, pH 4.5, 15 sec dwell time. Stage three tank conditions were 3% sodium erythorbate, 0.2% calcium chloride, 0.1.% EDTA, 35 sec dwell time.

Triplicate samples were collected at each sampling point. All samples were analyzed for aerobes and fluorescent pseudomonads.

Figure 2:
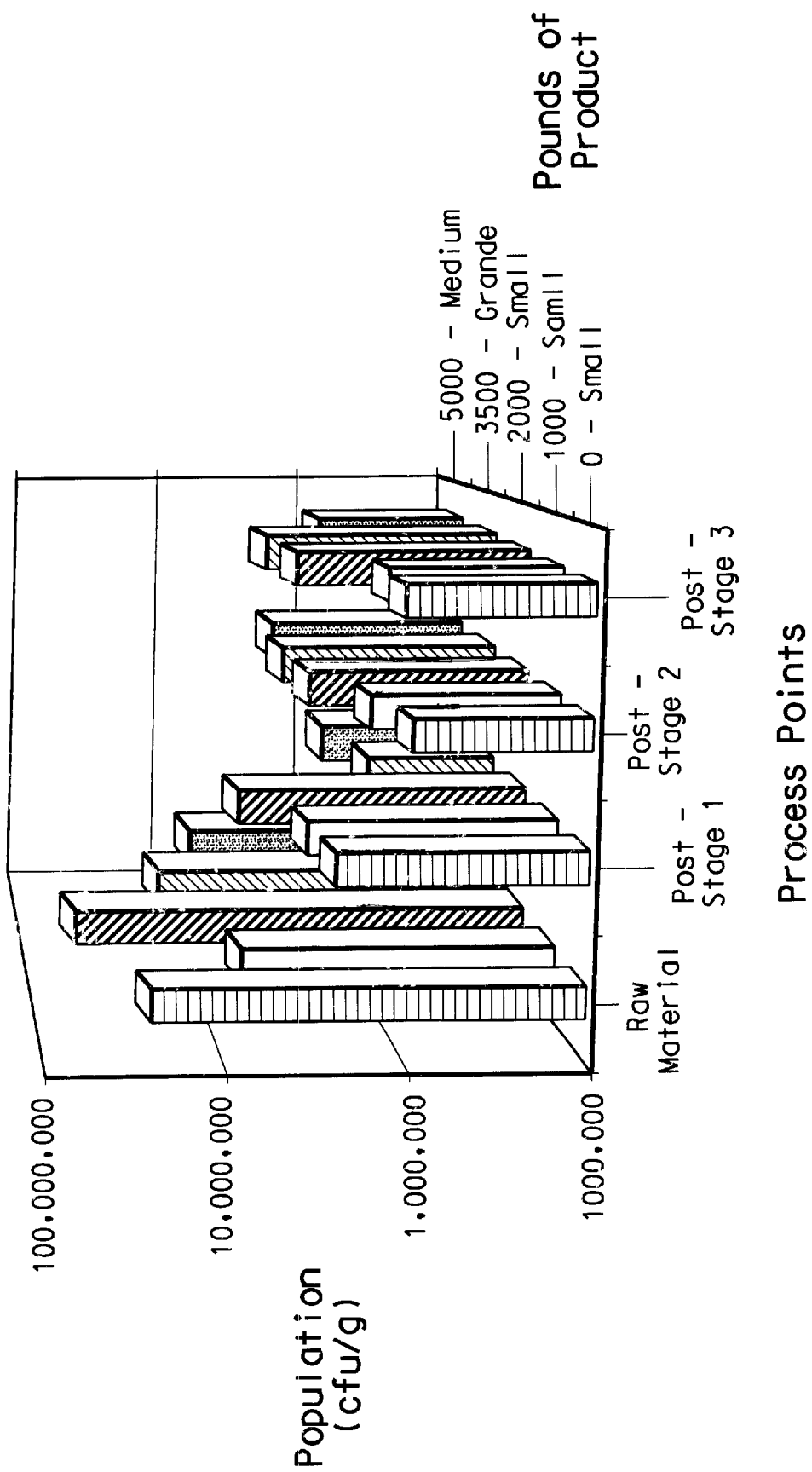

As shown in FIG. 1, the three-stage process resulted in an average aerobic population reduction of 17-fold in the washed mushrooms. An 11-fold reduction was found in pseudomonas population as reflected in FIG. 2.

We claim:

1. A method for preserving mushrooms comprising the steps of:
   contacting the mushrooms with an aqueous anti-microbial solution having a pH of from about 10.5 to about 11.5;
   rinsing the mushrooms at least once with at least one aqueous pH neutralizing buffer solution comprising organic acid and at least one salt of an organic acid and substantially free from erythorbic acid and sodium erythorbate; and
   contacting the mushrooms at least once with at least one solution comprising a browning inhibitor and a chelating agent.

2. A method of claim 1 wherein the anti-microbial solution comprises at least one of sodium bicarbonate, sodium carbonate and sodium hydroxide.

3. A method of claim 2 wherein the anti-microbial solution comprises from about 0.3% to about 0.5% by weight sodium carbonate and from about 0.05% to about 0.10% by weight sodium bicarbonate.

4. A method of claim 3 wherein the contacting with an anti-microbial solution is carried out for from about 20 to about 40 seconds at about 25° C.

5. A method of claim 1 wherein the browning inhibitor is selected from the group consisting of sodium erythorbate, erythorbic acid, ascorbic acid, calcium ascorbate and L-cysteine.

6. A method of claim 1 wherein the organic acid and salt of an organic acid comprise citric acid and sodium citrate, respectively.

7. A method of claim 6 wherein the rinsing step is carried out with a pH of about from 3.0 to 5.0 for about from 10 to 30 seconds.

8. A method of claim 7 wherein the browning inhibitor and chelating agent comprise sodium erythorbate and calcium disodium EDTA, respectively.

9. A method of claim 8 wherein the solution used in the anti-browning treating step further comprises calcium chloride and the contacting is carried out for about 20 to about 40 seconds.

10. A method of claim 9 wherein the solution in at least one step further includes an antifoaming or defoaming solution.

11. A method of claim 10 wherein the antifoaming solution comprises at least one silicon emulsion defoamer or antifoam.

12. A method of claim 6 wherein the solution used in the treating step further comprises calcium chloride.

13. A method of claim 12 wherein the solution in at least one treating step further includes an antifoaming or defoaming solution.

14. A method of claim 6 wherein the contacting is carried out for about 20 to about 40 seconds.

15. A method of claim 14 wherein the antifoaming solution comprises at least one silicon emulsion defoamer or antifoam.

16. A method of claim 15 wherein said organic acid comprises about from 0.4% to about 0.6% by weight citric acid and said salt of said organic acid comprises from about 0.6% to about 0.8% by weight sodium citrate with a pH of about from 3.0 to 5.0.

17. A method of claim 16 wherein said browning inhibitor is at least one selected from the group consisting of sodium erythorbate, erythorbic acid, ascorbic acid, calcium ascorbate and L-cysteine hydrochloride.

18. A method of claim 15 wherein the anti-browning step solution has a pH from about 6.5 to about 7.5.

19. A method of claim 18 wherein the antifoaming solution comprises at least one silicon emulsion defoamer or antifoam.

20. A method of claim 19 wherein the anti-microbial solution comprises from about 0.3% to about 0.5% by weight sodium carbonate and from about 0.05% to about 0.10% by weight sodium bicarbonate.

21. A method of claim 20 wherein the solution in at least one contacting step further includes an antifoaming or defoaming solution.

22. A method of claim 15 wherein the anti-microbial solution comprises at least one of sodium bicarbonate, sodium carbonate and sodium hydroxide.

23. A method of claim 22 wherein the contacting with an anti-microbial is carried out for about from 20 to about 40 seconds at a temperature of about 25° C.

24. A method of claim 23 wherein the antifoaming solution comprises at least one silicon emulsion defoamer or antifoam.

25. A method of claim 24 wherein the browning inhibitor and chelating agent comprise sodium erythorbate and calcium disodium EDTA, respectively, with a pH from about 6.8 to about 7.5.

26. A method of claim 25 wherein the antifoaming solution comprises at least one silicon emulsion defoamer or antifoam.

27. A method for preserving mushrooms comprising the steps of:
  contacting the mushrooms with an anti-microbial solution having a pH from about 10.5 to about 11.5;
  rinsing the mushrooms at least once with at least one aqueous pH neutralizing buffer solution comprising citric acid and sodium citrate and substantially free from erythorbic acid and sodium erythorbate; and
  treating the mushrooms at least once with at least one solution comprising a browning inhibitor and a chelating agent.

28. A method of claim 27 wherein said rinsing is carried out with a pH of about from 4.0 to 4.5 for about from 10 to 20 seconds.

29. A method of claim 28 wherein said chelating agent comprises calcium disodium EDTA.

30. A method of claim 29 wherein the solution in at least one step further includes an antifoaming or defoaming solution.

31. A method for preserving mushrooms comprising the steps of:
  contacting the mushrooms with an anti-microbial solution comprising sodium bicarbonate, sodium carbonate and sodium hydroxide, the solution having a pH from about 10.5 to about 11.5;
  rinsing the mushrooms at least once with at least one aqueous pH neutralizing buffer solution of at least one organic acid and at least one salt of an organic acid and substantially free from erythorbic acid and sodium erythorbate; and
  treating the mushrooms at least once with at least one solution comprising a browning inhibitor and a chelating agent with a pH from about 6.5 to about 7.5 and a divalent cation.

32. A method of claim 31 wherein the solution in at least one step further includes an antifoaming or defoaming solution.

* * * * *

UNITED STATES PATENT AND TRADEMARK OFFICE
Certificate

Patent No.6,500,476 B1                                                                                                  Patented: December 31, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Stefan T. Martin, Flourtown, PA (US); Howard S. Kravitz, Wayne, PA (US); William R. Romig, Morristown, NJ (US); Robert B. Beelman, State College, PA (US); and Eric M. Duncan, Worcester, England (UK).

Signed and Sealed this Seventh Day of May 2013.

D. LAWRENCE TARAZANO
*Supervisory Patent Examiner*
Art Unit 1791
Technology Center 1700